(12) United States Patent
Harthun et al.

(10) Patent No.: US 6,894,198 B2
(45) Date of Patent: May 17, 2005

(54) GRANULAR AKALI METAL ALKOXIDES AND ALKALINE EARTH METAL ALKOXIDES

(75) Inventors: Andreas Harthun, Mömbris (DE); Christoph Theis, Niederkassel (DE); André Noppe, Sankt Augustin (DE); Josef Metz, Marl (DE)

(73) Assignee: Degussa AG, Duesseldorf (DE)

( * ) Notice: Subject to any disclaimer, the term of this patent is extended or adjusted under 35 U.S.C. 154(b) by 210 days.

(21) Appl. No.: 10/270,114

(22) Filed: Oct. 15, 2002

(65) Prior Publication Data

US 2003/0078457 A1 Apr. 24, 2003

(30) Foreign Application Priority Data

Oct. 15, 2001 (DE) .......................... 101 50 328

(51) Int. Cl.⁷ ...................... C07C 31/30; C07C 31/38
(52) U.S. Cl. ...................... 568/851; 568/700; 568/821; 568/822; 568/823; 568/824; 568/825; 568/826; 568/838; 568/839; 568/840; 568/875

(58) Field of Search .................... 568/700, 821, 568/822, 823, 824, 825, 826, 838, 839, 840, 875, 851

(56) References Cited

U.S. PATENT DOCUMENTS 4,529,817 A * 7/1985 Stopp et al. ................ 562/423
4,946,653 A    8/1990 Stopp et al.
5,567,665 A   10/1996 Wagner et al.
6,297,188 B1 * 10/2001 Schork et al. .............. 502/171

FOREIGN PATENT DOCUMENTS

| CH | 451 197   | 5/1968 |
| DE | 199 56 558 | 6/2001 |
| EP | 0 089 565 | 9/1983 |
| EP | 0 600 282 | 6/1994 |
| EP | 0 997 451 | 5/2000 |

* cited by examiner

*Primary Examiner*—Elvis O. Price
(74) *Attorney, Agent, or Firm*—Oblon, Spivak, McClelland, Maier & Neustadt, P.C.

(57) ABSTRACT

An alkali metal alkoxide or alkaline earth metal alkoxide in granular form.

10 Claims, No Drawings

GRANULAR AKALI METAL ALKOXIDES AND ALKALINE EARTH METAL ALKOXIDES

BACKGROUND OF THE INVENTION

1. Field of the Invention

The present invention relates to alkali metal and alkaline earth metal alkoxides in granular form.

2. Description of the Background

Alkoxides are used for a wide variety of applications. Alkoxides are used in aldol addition reactions, esterification/transesterification reactions, malonic ester syntheses, ether formations, as well as being generally used as a base in other reactions. In addition, alkoxides are widely used in the food industry, for example in margarine production or vitamin A synthesis, in the pharmaceutical industry, for example in the preparation of antibiotics, analgesics, chemotherapy drugs and anti-epileptics, in the agrochemicals industry, for example in the production of herbicides and fungicides, and in many other fields, for example in the production of optical brighteners, UV absorbers and photoinitiators.

For these purposes, the alkoxides are generally used in the form of their alcoholic solutions or, if the alcohol is undesirable and it is technically and logistically possible, in powder form if available.

A disadvantage in the handling of an alkoxide powder is its tendency to form fine dust during packaging and transfer operations, because this dust is hazardous to human beings and machinery because of the strongly corrosive action of the alkoxides and because of the case with which they spontaneously ignite in the atmosphere.

When alkoxides are used as reactants, exothermic reactions which frequently occur and are difficult to control also represent an additional, not inconsiderable process risk. These hazard potentials require a very high outlay in terms of process engineering and apparatus.

SUMMARY OF THE INVENTION

Accordingly, one object of the invention is to provide alkali metal and alkaline earth metal alkoxides in a form which does not have the indicated disadvantages, in particular the formation of corrosive fine dust during handling.

Briefly, this object and other objects of the present invention as hereinafter will become more readily apparent can be attained by the preparation of an alkoxide in granular form.

DETAILED DESCRIPTION OF THE PREFERRED EMBODIMENTS

It has been found that alkali metal alkoxides and alkaline earth metal alkoxides of alcohols having from 1 to 12, preferably from 1 to 6, carbon atoms, can be converted by means of particular process engineering measures into a solid granular form by means of which the risks on handling the abovementioned alkoxides and their use in customary reactions can be considerably reduced and minimized. The invention therefore provides alkali metal alkoxides and alkaline earth metal alkoxides of alcohols having from 1 to 12, preferably from 1 to 6, carbon atoms in granular form preferably produced by the fluidized-bed spray granulation process. As a coarsely particulate material, the alkoxides in granular form are easy to store, convey, meter and mix, since they do not dust, do not agglomerate and do not tend to bridge in this form of solid.

Alkali metal cations components which can be present in the alkoxide include lithium, sodium and/or potassium ions. Preferred alkali metal alkoxides are, in particular, sodium and potassium alkoxides.

Alkaline earth metal cations which can be present in the alkoxide include magnesium and/or calcium ions. Preferred alkaline earth metal alkoxides are, in particular, magnesium alkoxides.

The alcohol radical in the alkoxide is derived from an aliphatic, unbranched or branched, saturated or unsaturated alcohol having from 1 to 12, preferably from 1 to 6, very particularly preferably from 1 to 4, carbon atoms.

Preferred radials are the radicals derived from methanol, ethanol, npropanol, isopropanol, allyl alcohol, n-butanol, isobutanol, tert-butanol, amyl alcohol (pentanol) including the various isomers of pentanol and hexanol including the various isomers of hexanol. However, the invention relates in particular to granular alkoxides of methanol, of ethanol, of propanol and of butanol in their various isomeric forms. This listing is, however, merely by way of example and does not restrict the scope of the invention.

The alkoxide content of the granular material is 50–100% by weight, preferably 90–99% by weight and in particular >98% by weight. As a process engineering measure for producing the granular materials, fluidized-bed spray granulation can be employed. The shape and diameter of the granules can be set and varied by means of the production and drying conditions. The granules are preferably present in an asymmetric, approximately spherical form.

The diameter of the granules extends from microns to the centimeter range. Preference is given to producing granules having a diameter ranging from 100 $\mu$m to 10 mm. Since the granule size depends essentially on the granulation conditions, the quoted granule size does not constitute a confining limitation of the invention.

As a result of the granular form, the flowability index (ffc) is greatly increased compared to a pulverulent alkoxide, which leads to considerable advantages in handling.

Furthermore, the speed of dissolution is determined, inter alia, by the granule size and this makes the desired reaction more uniform. As a result, exothermic chemical reactions can be controlled significantly more readily.

Although the spontaneous ignition temperature (without time limit) is not reduced, a dust explosion can be ruled out for the granular material because virtually no dust occurs in transfer and packaging operations.

The most widely used of the solid alkali metal alkoxides is sodium methoxide. For this reason, the materials properties of sodium methoxide powder and granular sodium methoxide are compared below by way of example. However, the property differences are generally present for the granular alkoxides as specified in the above description and therefore the scope of the invention should not be understood to apply exclusively to sodium methoxide.

|  | Sodium methoxide powder | Granular sodium methoxide |
|---|---|---|
| Bulk density [g/l] | ca. 500 | ca. 400 |
| Tamped density [g/l] | ca. 645 | ca. 410 |
| Densification [%] | 22.5 | 2.5 |
| Flowability index (ffc) | 5.19 | 18.74 |
| Specific surface area [m2/g] (DIN 66131) | 6.4 | 17 |

-continued

|  | Sodium methoxide powder | Granular sodium methoxide |
|---|---|---|
| Spontaneous ignition temperature in the presence of air [° C.] | 55–60 | 50–55 |

It can be observed from the data in the table that the granular sodium methoxide is a solid which has significantly more advantageous properties in terms of handling when compared to sodium methoxide powder. The indicated, lower bulk density of the granular material is essentially dependent on the granule diameter which can in turn be altered by variation of the granulation conditions. The granular material examined has an average diameter of 2 mm. However, these data are purely by way of example and should not be interpreted as a limitation of the scope of the invention pertaining to granule diameter or the industrially achievable bulk density of the granular alkoxides.

The granular material has considerably better flow properties than powder and in a tamping test undergoes a compaction of only 2.5%. In contrast, the powder is densified by 22.5%.

According to the invention, the granular alkoxide provides a form of solid alkoxide which has considerably better storage, conveying and metering properties than the corresponding powder.

The dissolution rate of the solid sodium methoxide in different alcohols is summarized below. For this purpose, 25 g of solid are stirred under inert gas conditions in 100 g of ethanol, and 40 g of solid are stirred in 100 g of methanol.

|  | Methanol | Ethanol |
|---|---|---|
| Sodium methoxide powder [min] | 6 | 10 |
| Granular sodium methoxide [min] | 16 | 12 |

A comparison of the dissolution rates of sodium methoxide powder and granules clearly shows that the granular material dissolves more slowly at the same stirring rate than does the corresponding powder. However, this materials property of the granular material has novel advantages in batchwise exothermic reactions. A reduced dissolution rate of the alkoxide allows the reaction with the alkoxide to proceed more uniformly. This effect is observed even in polar, protic solvents in which alkoxides dissolve to only a slight extent.

An example is the carbonylation of propionic esters in dimethylformamide. Owing to the extremely high CO uptake and evolution of heat which occur, this reaction is a particularly suitable model reaction.

Having generally described this invention, a further understanding can be obtained by reference to certain specific examples which are provided herein for purposes of illustration only and are not intended to be limiting unless otherwise specified.

EXAMPLES

Comparative Example
Carbonylation of Ethyl Propionate Using Sodium Methoxide Powder The carbonylation of ethyl propionate using sodium methoxide powder in dimethylformamide displays a temperature maximum of 80° C., while at the same time a pressure drop of about 10 bar occurs in the autoclave and the volume flow of CO is simultaneously increased by 500%.

Example of the Invention
Carbonylation of Ethyl Propionate Using Granular Sodium Methoxide The carbonylation of ethyl propionate using granular sodium methoxide proceeds considerably more moderately. The maximum temperature is only 70° C. with an insignificant drop in pressure and a maximum volume flow of CO of 20% of the maximum volume flow of CO in the comparative example.

The uniform way in which the reaction proceeds surprisingly has no influence on the space-time yield.

The example of the carbonylation of ethyl propionate using granular sodium methoxide makes it clear that the granular alkoxide not only has advantages in mechanical handling but also displays considerable advantages in conducting exothermic reactions.

The disclosure of German priority application Serial No. 101 50 328.8 filed Oct. 15, 2001 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A granular alkali metal alkoxide.

2. The granular alkoxide as claimed in claim 1, wherein the diameter of the granules of alkoxide is determined by means of the production and drying conditions employed in a given process of preparing the alkoxide.

3. The granular alkoxide as claimed in claim 1, wherein the alcohol portion of the alkoxide is derived from an aliphatic, saturated or unsaturated alcohols having from 1 to 12 carbon atoms.

4. The granular alkoxide as claimed in claim 3, wherein the number of carbon atoms ranges from 1 to 6.

5. The granular alkoxide as claimed in claim 4, wherein the number of carbon atoms ranges from 1 to 4.

6. The granular alkoxide as claimed in claim 3, wherein the alcohol is selected from the group consisting of methanol, ethanol, propanol, isopropanol, allyl alcohol, butanol, isobutanol, tert-butanol, pentanol, isomers of pentanol, hexanol and isomers of hexanol.

7. The granular alkoxide as claimed in claim 1, wherein the cationic component of the alkoxide is sodium or potassium ion.

8. The granular alkoxide as claimed in claim 1, wherein the granules of alkoxide have a diameter ranging from 100 $\mu$m to 10 mm.

9. The granular alkoxide as claimed in claim 1, which has an alkoxide content of 50–100% by weight.

10. The granular alkoxide as claimed in claim 9, which has an alkoxide content of >98% by weight.

* * * * *

UNITED STATES PATENT AND TRADEMARK OFFICE
CERTIFICATE OF CORRECTION

PATENT NO.    : 6,894,198 B2
DATED         : May 17, 2005
INVENTOR(S)   : Andreas Harthun et al.

It is certified that error appears in the above-identified patent and that said Letters Patent is hereby corrected as shown below:

Title page,
Item [54], Title, should read:
-- GRANULAR ALKALI METAL ALKOXIDES AND ALKALINE EARTH METAL ALKOXIDES --

Column 1,
Line 32, "case" should read -- ease --.

Signed and Sealed this

Ninth Day of August, 2005

JON W. DUDAS
*Director of the United States Patent and Trademark Office*